(12) United States Patent  
Baker

(10) Patent No.: US 10,231,766 B2
(45) Date of Patent: Mar. 19, 2019

(54) DISTAL RADIUS PLATE

(71) Applicant: Smith & Nephew, Inc., Memphis, TN (US)

(72) Inventor: Charles R. Baker, Lakeland, TN (US)

(73) Assignee: SMITH & NEPHEW, INC., Memphis, TN (US)

( * ) Notice: Subject to any disclaimer, the term of this patent is extended or adjusted under 35 U.S.C. 154(b) by 295 days.

(21) Appl. No.: 15/107,766

(22) PCT Filed: Dec. 23, 2014

(86) PCT No.: PCT/US2014/072108
§ 371 (c)(1),
(2) Date: Jun. 23, 2016

(87) PCT Pub. No.: WO2015/100304
PCT Pub. Date: Jul. 2, 2015

(65) Prior Publication Data
US 2016/0317205 A1 Nov. 3, 2016

Related U.S. Application Data

(60) Provisional application No. 61/920,352, filed on Dec. 23, 2013.

(51) Int. Cl.
*A61B 17/80* (2006.01)
(52) U.S. Cl.
CPC ...... *A61B 17/8057* (2013.01); *A61B 17/8052* (2013.01); *A61B 17/8061* (2013.01)
(58) Field of Classification Search
CPC .................. A61B 17/8052; A61B 17/8061
See application file for complete search history.

(56) References Cited

U.S. PATENT DOCUMENTS

2005/0240187 A1 10/2005 Huebner et al.
2006/0004362 A1 1/2006 Patterson
(Continued)

FOREIGN PATENT DOCUMENTS

CN 202173466 U 3/2012
WO 2012050424 A1 4/2012

OTHER PUBLICATIONS

Communication pursuant to Rule 164(2)(b) and Article 94(3) EPC for EP14824330.6 dated Sep. 6, 2017.
(Continued)

*Primary Examiner* — Olivia C Chang

(57) ABSTRACT

A bone plate fixation system for fixation of the distal radius bone includes a bone plate having an elongate shaft portion and a triangular-shaped head portion, with each portion defining a number of bone screw openings extending therethrough for receipt of bone screws. The triangular-shaped head portion may define an elongate visualization window having a window length extending across a width of the bone plate. At least some of the openings include flexible fins protruding radially inward into the opening and deflectable by the head of a bone screw to retain the bone screw in position within the opening. In one embodiment, the bone plate has an outer perimeter that is substantially symmetrical relative to a longitudinal axis of the bone plate. In another embodiment, the elongate shaft portion includes an elongate slot having a length extending along the longitudinal axis. In a further embodiment, the triangular-shaped head portion includes an elongate aperture having a length extending along the longitudinal axis.

27 Claims, 3 Drawing Sheets

(56) References Cited

U.S. PATENT DOCUMENTS

| | | | |
|---|---|---|---|
| 2006/0259039 A1 | 11/2006 | Pitkanen et al. | |
| 2008/0140130 A1 | 6/2008 | Chan et al. | |
| 2008/0300637 A1* | 12/2008 | Austin | A61B 17/74 606/290 |
| 2009/0143824 A1 | 6/2009 | Austin et al. | |
| 2009/0228047 A1 | 9/2009 | Derouet et al. | |
| 2011/0218534 A1* | 9/2011 | Prandi | A61B 17/80 606/71 |
| 2012/0290016 A1 | 11/2012 | Kumar | |
| 2012/0323284 A1 | 12/2012 | Baker et al. | |
| 2012/0078253 A9 | 3/2013 | Huebner et al. | |
| 2013/0172943 A1 | 7/2013 | Austin et al. | |

OTHER PUBLICATIONS

International Search Report; European Patent Office; International Appiication No. PCT/US2014/072108; dated Jun. 10, 2015; 6 pages.
Written Opinion of the International Searching Authority; European Patent Office; International Application No. PCT/US2014/072108; dated Jun. 10, 2015; 8 pages.
First Office Action for Chinese Patent Application No. 201480076220.0 dated Apr. 16, 2018. English translation provided.

* cited by examiner

DISTAL RADIUS PLATE

CROSS REFERENCE TO RELATED APPLICATIONS

This application is a U.S. National Phase of International PCT Application No. PCT/US2014/072108 filed on Dec. 23, 2014, which claims the benefit of U.S. Provisional Application No. 61/920,352 filed Dec. 23, 2013, the contents of each application incorporated herein by reference in their entirety.

FIELD OF THE INVENTION

The present invention relates generally to orthopedic plates, and more particularly but not exclusively relates to orthopedic distal radius plates.

BACKGROUND

Bone plate fixation systems for repairing bone fractures are commonly used in a variety of orthopedic applications. These fixation systems include bone plates that may be provided in many shapes, sizes and configurations. In cases where a bone is severely comminuted or if bone segments are missing, the use of a bone plate fixation system promotes healing of the fracture by providing a rigid fixation or support structure between the bone and the plate. In some instances, the bone plate fixation system is designed for use in treating a particular type of bone or a specific portion or region of a bone, and may also be provided with specific structures and/or features that facilitate treatment of the bone and provide the necessary support and stabilization to facilitate healing.

There remains a need for an improved bone plate fixation system for treatment of the distal radius bone. The present invention addresses this need and provides other benefits and advantages in a novel and non-obvious manner.

SUMMARY

While the actual nature of the invention covered herein can only be determined with reference to the claims appended hereto, certain forms of the invention that are characteristic of the embodiments disclosed herein are described briefly as follows.

In general, a novel orthopedic bone plate is provided which presents a stable connection between the bone plate and the distal radius bone, and which includes structures and features that facilitate treatment of the bone to provide support and stabilization to facilitate healing.

In one form of the invention, a bone plate fixation system is provided which includes a plurality of bone screws, each including a screw head and a threaded shank extending from the screw head and adapted for anchoring within bone, and a bone plate extending along a central longitudinal axis and having a plate body defining an outer perimeter that is substantially symmetrical relative to the longitudinal axis, the plate body including an elongate shaft portion and a triangular-shaped head portion extending from the elongate shaft portion. The plate body includes a number of bone screw openings extending therethrough, each having an inner surface and a plurality of flexible fins integrally connected to and protruding radially inward from the inner surface. The plurality of flexible fins are deflectable by the screw head of one of the bone screws inserted into a corresponding one of the bone screw openings to retain the bone screw in position within the corresponding opening relative to the plate body. The elongate shaft portion of the plate body includes a first plurality of the bone screw openings and an elongate slot having a slot length extending along the longitudinal axis. The triangular-shaped head portion of the plate body includes a second plurality of the bone screw openings and at least one fastener opening extending therethrough that does not include the plurality of flexible fins. The triangular-shaped head portion further includes an elongate visualization window extending therethrough and having a window length extending in a direction transverse to the longitudinal axis of the plate body.

In one embodiment of the bone plate fixation system, the screw head of at least some of the plurality of bone screws includes an external thread adapted to engage with the plurality of flexible fins of a corresponding one of the bone screw openings. In another embodiment, the plurality of flexible fins provide each of the plurality of bone screw openings with a star-shaped configuration.

In another embodiment, the triangular-shaped head portion of the plate body further includes an elongate aperture extending therethrough. In a further embodiment, the elongate aperture has an aperture length extending generally parallel with the longitudinal axis. In one variation, the aperture length of the elongate aperture in the triangular-shaped head portion extends in a direction substantially parallel with the slot length of the elongate slot in the elongate shaft portion. In yet another embodiment, the elongate slot in the elongate shaft portion is centered along the longitudinal axis and the elongate aperture in the triangular-shaped head portion is laterally offset from the longitudinal axis. In still another embodiment, the elongate slot in the elongate shaft portion has a slot width and the elongate aperture in the triangular-shaped head portion has an aperture width that is less than the slot width. In still yet another embodiment, the bone plate fixation system further includes a K-wire or pin positioned within and extending through the elongate aperture and adapted for anchoring in the bone.

In a further embodiment, the elongate visualization window is centered along the longitudinal axis and has a shape that is substantially symmetrical relative to the longitudinal axis. In another variation, the elongate visualization window has a window length extending in a direction substantially perpendicular to the longitudinal axis. In yet another variation, the elongate visualization window has a trapezoidal shape. In still another variation, the elongate visualization widow remains unobstructed when the plate body is attached to the bone to provide direct visualization of a portion of the bone through the plate body. In a further variation, the elongate visualization window is defined by a pair of substantially parallel bases extending along the window length, and a pair of non-parallel legs that extend substantially parallel with corresponding peripheral side surfaces defined by the triangular-shaped head portion of the plate body.

In a further embodiment, the elongate slot in the elongate shaft portion of the plate body and the at least one fastener opening in the triangular-shaped head portion are each centered along the longitudinal axis. In another embodiment, a first plurality of the bone screw openings in the triangular-shaped head portion are arranged substantially symmetrical relative to the longitudinal axis, and the second plurality of the bone screw openings in the elongate shaft portion are each substantially centered along the longitudinal axis. In yet another embodiment, the first plurality of the bone screw openings in the triangular-shaped head portion are sized, shaped and configured substantially identical to the second plurality of the bone screw openings in the elongate shaft portion. In a further embodiment, the elongate shaft portion of the plate body includes three or more of the bone screw openings. In still yet another embodiment, the triangular-shaped head portion has a convex distal end surface that is substantially centered relative to the longitudinal axis.

In another form of the invention, a bone plate fixation system is provided which includes a plurality of bone screws that each have a screw head and a threaded shank extending from the screw head and adapted for anchoring within bone, and a bone plate extending along a longitudinal axis and having a plate body including an elongate shaft portion and a triangular-shaped head portion extending from the elongate shaft portion. The plate body includes a number of bone screw openings extending therethrough and each having an inner surface and a plurality of flexible fins integrally connected to and protruding radial inward from the inner surface. The plurality of flexible fins are deflectable by the screw head of one of the bone screws inserted into a corresponding one of the bone screw openings to retain the bone screw in position within the corresponding opening relative to the plate body. The elongate shaft portion of the plate body includes a first plurality of the bone screw openings and a first elongate slot having a slot length extending generally parallel with the longitudinal axis. The triangular-shaped head portion of the plate body includes a second plurality of the bone screw openings and a second elongate slot having a slot length extending generally parallel with the longitudinal axis. The triangular-shaped head portion further includes an elongate visualization window extending therethrough and having a window length extending in a direction transverse to the longitudinal axis of the plate body.

In one embodiment of the bone plate fixation system, the first elongate slot in the elongate shaft portion is centered along the longitudinal axis, and the second elongate slot in the triangular-shaped head portion is laterally offset from the longitudinal axis. In another embodiment, the first elongate slot in the elongate shaft portion has a first slot width and the second elongate slot in the triangular-shaped head portion has a second slot width that is less than the first slot width. In yet another embodiment, the bone plate fixation system further includes a fastener extending through the first elongate slot in the elongate shaft portion and adapted for anchoring within the bone, and a K-wire or pin extending through the second elongate slot in the triangular-shaped head portion and adapted for anchoring within the bone. In still another embodiment, the plate body defines an outer perimeter that is substantially symmetrical relative to the longitudinal axis.

In another embodiment, the screw head of at least some of the plurality of bone screws includes an external thread engaged with the plurality of flexible fins of a corresponding one of the bone screw openings. In yet another embodiment, the plurality of flexible fins provide each of the plurality of bone screw openings with a star-shaped configuration. In a further embodiment, the elongate visualization widow remains unobstructed when the plate body is attached to the bone to provide direct visualization of a portion of the bone through the plate body. In a further variation, the elongate visualization window is defined by a pair of substantially parallel bases extending along the window length, and a pair of non-parallel legs that extend substantially parallel with corresponding peripheral side surfaces defined by the triangular-shaped head portion of the plate body.

In a further embodiment, a first plurality of the bone screw openings in the triangular-shaped head portion are arranged substantially symmetrical relative to the longitudinal axis, and a second plurality of the bone screw openings in the elongate shaft portion are each substantially centered along the longitudinal axis. In another embodiment, the first plurality of the bone screw openings in the triangular-shaped head portion are sized, shaped and configured substantially identical to the second plurality of the bone screw openings in the elongate shaft portion. In still another embodiment, the triangular-shaped head portion has a convex distal end surface that is substantially centered relative to the longitudinal axis.

It is one object of the present invention to provide an improved orthopedic distal radius plate. Further embodiments, forms, features, aspects, benefits, objects, and advantages of the present invention will become apparent from the detailed description and figures provided herewith.

DESCRIPTION OF THE ILLUSTRATED EMBODIMENTS

Figure 1:
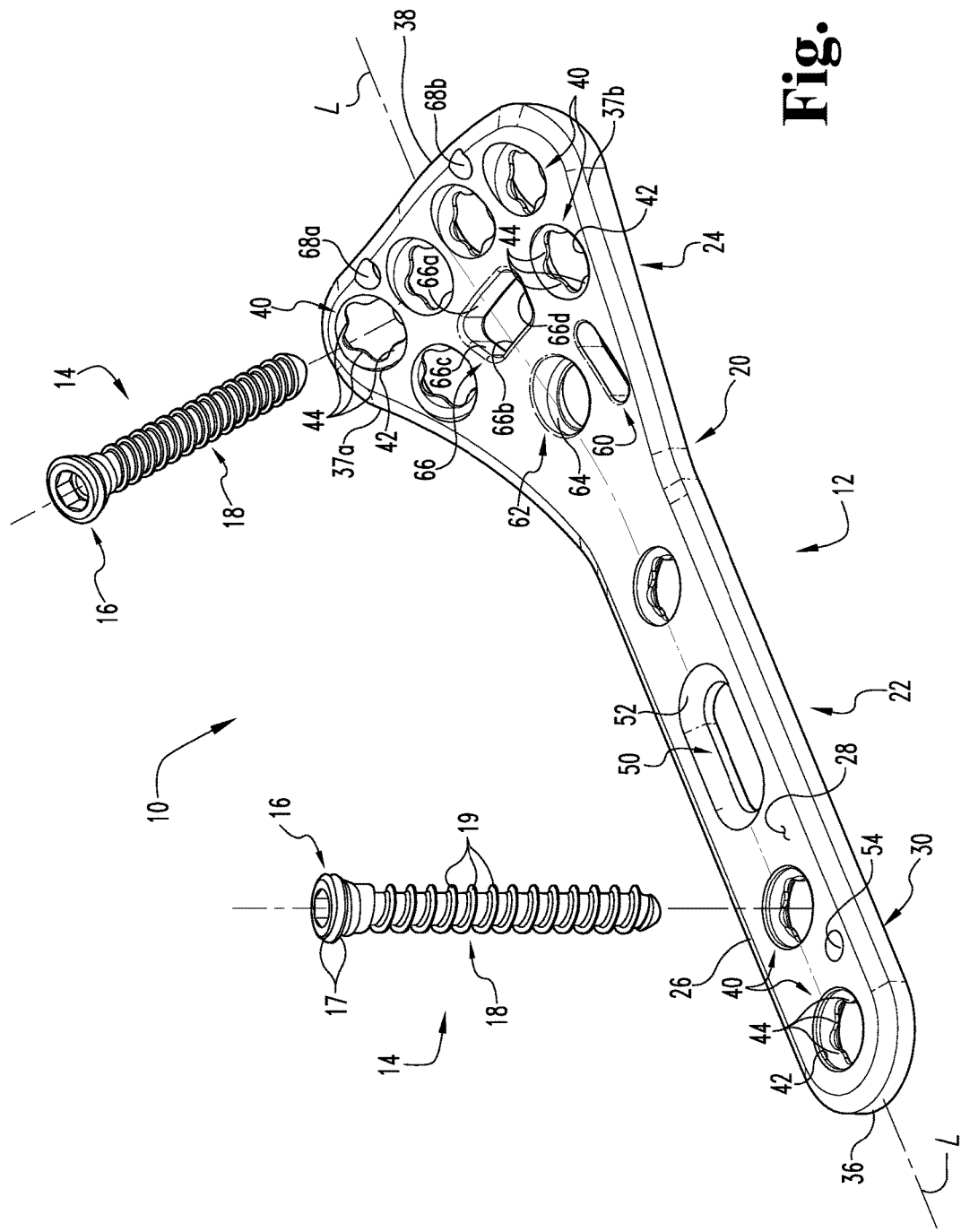
FIG. 1 is a perspective view of an orthopedic distal radius plate according to one form of the present invention.

For the purpose of promoting an understanding of the principles of the present invention, reference will now be made to the embodiments illustrated in the drawings and specific language will be used to describe the same. It will nevertheless be understood that no limitation on the scope of the invention is hereby intended. Any alterations and further modifications in the described embodiments, and any further applications of the principles of the invention as described herein are contemplated as would normally occur to one skilled in the art to which the invention relates.

The following descriptions and illustrations of non-limiting embodiments of the present invention are exemplary in nature, it being understood that the descriptions and illustrations related thereto are in no way intended to limit the inventions disclosed herein and/or their applications and/or uses.

The bone plate fixation system disclosed herein provides a stable connection between a bone and a bone plate using a plurality of fasteners that permit different angles to be obtained between the bone plate and the fastener. The fasteners also lock into the bone plate to prevent or at least inhibit fastener back out. While fastener receiving openings in the bone plate are located in fixed positions, the angle variability allows the surgeon to reach denser areas of bone or capture bone fragments that are in irregular positions such as, for example, in cases of severe fractures with highly fragmented bones. The bone plate fixation system also allows the surgeon to choose the angle at which the screw is inserted through, and rigidly affixed in, an opening in the plate. Moreover, the bone plate fixation system allows a surgeon to direct a fastener toward a bone fragment that is not necessarily located along the axis of the opening in the plate. The system also provides flexibility in the placement of the plate in relation to the bone fracture, and allows the surgeon to choose the angle at which the fastener is inserted into the plate, which in turn leads to better tailoring of the system to the specific nature and characteristics of the bone and bone fracture being treated.

Figure 2:
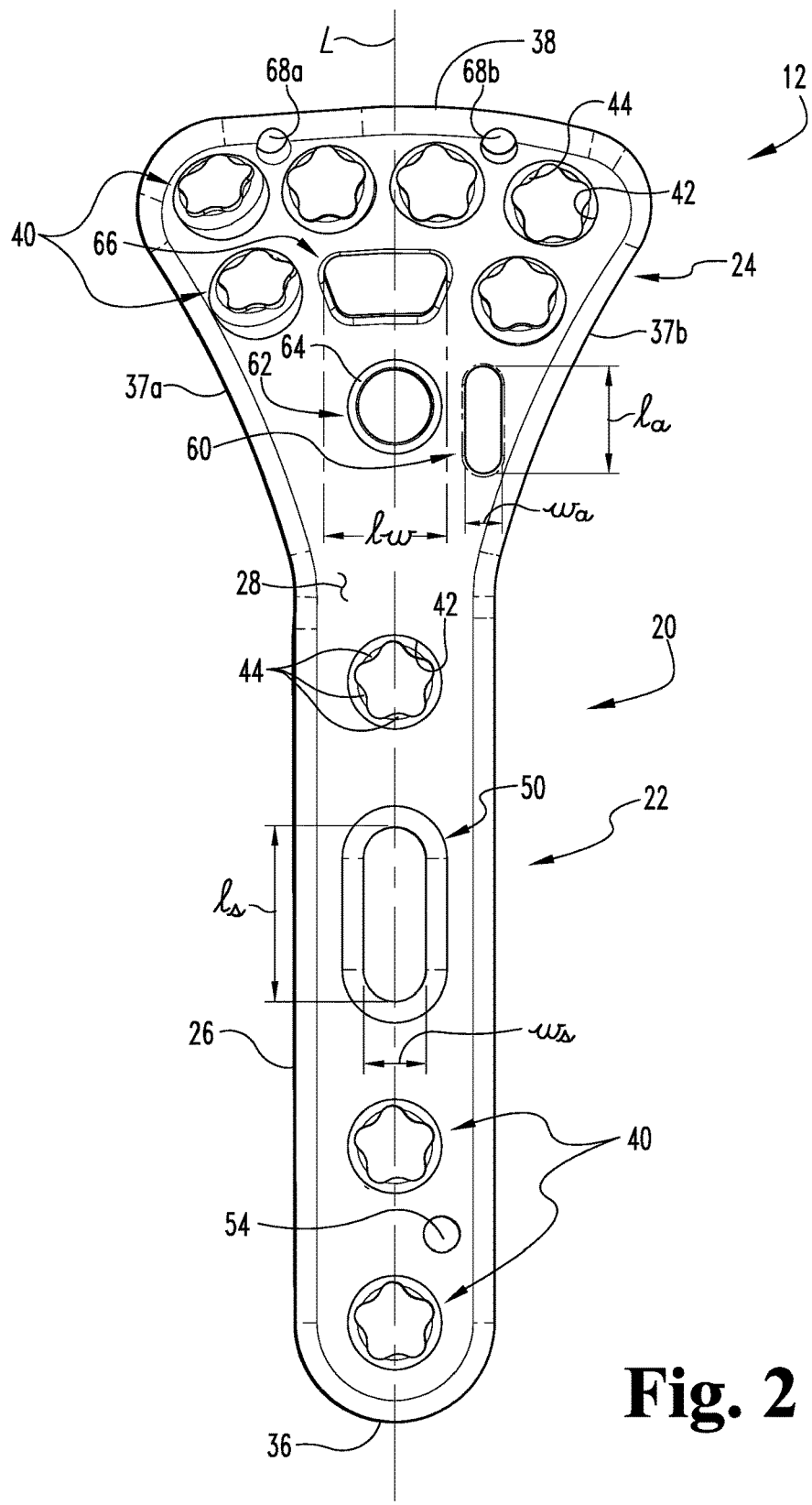
FIG. 2 is a top plan view of the orthopedic distal radius plate of FIG. 1.
Figure 3:
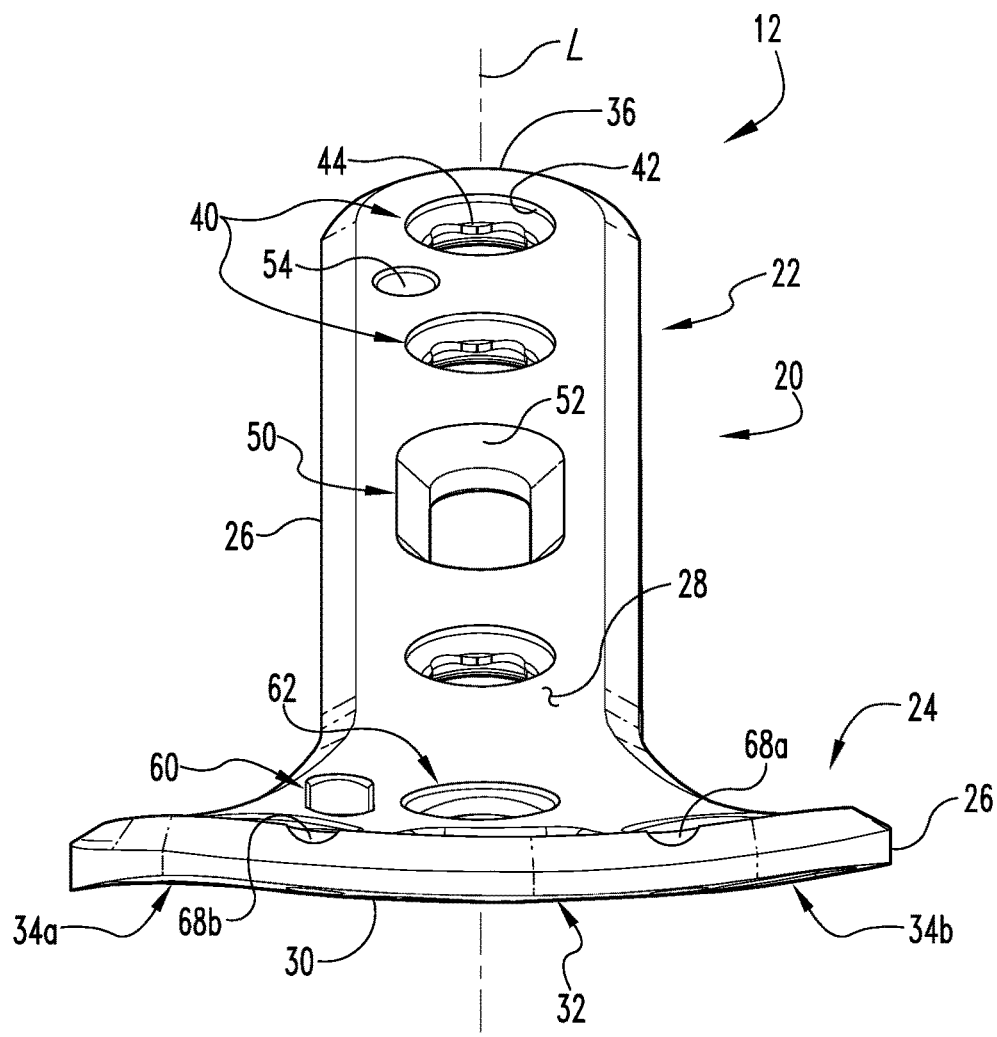
FIG. 3 is a distal end view of the orthopedic distal radius plate of FIG. 1.

Referring to FIGS. 1-3, shown therein is a bone plate fixation system 10 according to one form of the invention that generally includes a bone plate 12 and a plurality of bone anchors 14 that are configured to securely anchor the bone plate 12 to a bone. In the illustrated embodiment of the invention, the bone plate 12 is configured for fixation of fractures, non-unions and osteotomies of the radius bone, and more particularly the distal radius bone. However, it should be understood that the bone plate 12 may be configured for use in association with other orthopedic surgeries or procedures associated with other bones or joints requiring fixation in addition to the distal radius bone.

In the illustrated embodiment, the bone anchors 14 are configured as bone screws having a head portion 16 configured for engagement with the bone plate 12 and a threaded shank portion 18 configured for anchoring within bone. In one embodiment, the head portion 16 includes at least one anti-back out feature or external thread 17 that engages a portion of the bone plate 12 to prevent or inhibit displacement or back out of the bone anchor 14 from the bone plate 12. As will be described in further detail below, the anti-back out feature or external thread 17 is adapted to engage, associate with, or otherwise cooperate with fins or projections that extend radially inward into bone screw openings in the bone plate 12. In some embodiments, the anti-back out feature 17 may be provided as a continuous ridge or a non-continuous ridge, and may comprise a portion of a revolution, one complete revolution, multiple revolutions, a single lead, or multiple leads. Additionally or alternatively, the head portion 16 of bone screw 14 may include other features or elements that engage with and/or seat within corresponding features of the bone plate 12 to prevent or inhibit displacement or back out of the bone anchor 14 from the bone plate 12. For example, the head portion 16 may be provided with a series of dimples, ridges, bumps, textured areas, or any other surface features that engage with features of the bone plate 12. Additionally, the head portion 16 may be provided with a tool-receiving opening or recess that is sized and configured to receive a distal end of a driver instrument to drive the bone screw 14 into engagement with bone. The threaded shank portion 18 is provided with an external thread 19 configured for engagement with bone or bone tissue to anchor the bone screw 14 (and the bone plate 12) to the bone. In some embodiments, the external thread 19 formed about and extending along the shank portion 18 is courser (i.e., has a greater pitch) relative to the external thread 17 formed about the head portion 16. Additionally, the distal end of threaded shank 18 may be fluted or may include another type of cutting element to provide the bone screw 14 with self-tapping or self-drilling capabilities.

Although the bone anchors 14 are illustrated and described as bone screws, it should be appreciated that other types and configurations of bone anchors or fasteners are also contemplated for use in association with the bone plate 12 to secure the bone plate 12 to the underlying bone. For example, in other embodiments of the bone anchors 14, the shank portion 18 may be provided as a smooth, non-threaded shank such as, for example, a pin or peg. Other embodiments of the bone anchors 14 are also contemplated where the head portion 16 is smooth and is not provided with an anti-back out feature or external thread 17. Additionally, it should be understood that the bone anchors 14 may be made out of any suitable biocompatible material including, for example, biocompatible metallic materials such as stainless steel or titanium. However, it should also be understood that the bone anchors 14 may be formed of other suitable materials including other metallic materials, ceramic materials, composite materials, and resorbable or non-resorbable plastic or polymeric materials.

In the illustrated embodiment, the bone plate 12 includes a plate body 20 extending along a central longitudinal axis L and generally including an elongate shaft portion 22 and a triangular-shaped head portion 24 extending from the elongate shaft portion 22. The plate body 20 may be formed of any suitable material having appropriate strength, manufacturability, autoclavability, and other desired performance characteristics. Suitable materials include, for example, titanium, stainless steel, cobalt chrome, polyetheretherketone (PEEK), polyethylene, ultra high molecular weight polyethylene (UHMWPE), resorbable polylactic acid (PLA), polyglycolic acid (PGA), combinations or alloys of such materials, or any other appropriate material that has sufficient strength to provide fixation to the bone while also having sufficient biocompatibility for implantation within the body.

In the illustrated embodiment, the plate body 20 defines an outer perimeter 26 that is substantially symmetrical relative to the longitudinal axis L, and also includes an upper plate surface 28 and a lower bone engagement surface 30 that is shaped and configured to generally conform to the outer surface of the underlying bony structure (i.e., the distal radius bone and/or the radial head). In one embodiment, the lower bone engagement surface 30 may have an arcuate or curved shape that generally conforms with the outer contour of the underlying bone. Additionally, the lower bone engagement surface 30 may have a convex curvature and/or a concave curvature. As illustrated in FIG. 3, in the illustrated embodiment of the plate body 20, the lower bone engagement surface 30 of the triangular-shaped head portion 24 is provided with a convex curvature 32 and one or more concave curvatures 34a, 34b located on either side of the convex curvature 32. Although the curvatures 32 and 34a, 34b are illustrated as extending along a width of the plate body 20 (i.e., in a direction generally perpendicular to the longitudinal axis L), it should be appreciated that the lower bone engagement surface 30 may be provided with curvatures that extend generally along a length of the plate body 20 (i.e., in a direction along the longitudinal axis L). Additionally, in the illustrated embodiment, the plate body 20 includes a proximal end surface 36 having a convex profile or curvature, and a distal end surface 38 also having a convex curvature or profile, and with the convex profiles of the end surfaces 36, 38 each being substantially centered relative to the longitudinal axis L and generally symmetrical relative to the longitudinal axis L. As should be appreciated, the symmetrical shape and configuration of the plate body 20 allows the same bone plate 12 to be used for right-side and left-side applications.

In one embodiment, the bone plate 12 combines features of polyaxial fixation with a low profile and lower bone engagement surface contouring that enables the plate body 20 to conform closely to the underlying bone. The lower surface contouring not only minimizes prominence of the plate body 20 (and therefore reduces potential for soft tissue irritation), but also facilitates fracture reduction and stabilization by allowing, if desired, mid-portions of the plate body to be compressed to bone to achieve a buttressing effect. This effect helps, among other things, to resist torque and bending during fracture healing. Once securely fixed in place using such compression techniques, the plate body produces a buttress effect to the fracture site to help prevent loss of reduction and enhance overall fracture fixation.

Lower surface contouring also allows additional screw convergence in metaphyseal areas of the bone.

In the illustrated embodiment, the plate body 20 includes a number of bone screw openings 40 extending through the thickness of the plate from the upper plate surface 28 to the lower bone engagement surface 30. The bone screw openings 40 are each configured to receive a corresponding one of the bone screws 14 therethrough which in turn extend into bone to securely anchor the plate body 20 to the bone. Each of the bone screw openings 40 has an inner surface 42 and a plurality of flexible fins 44 integrally connected to and protruding radially inward from the inner surface 42. The primary purpose of fins 44 is to engage the anti-back out feature or external thread 17 on the head portion 16 of the bone screw 14 in order to secure the bone screw 14 at a desired position and at a desired angle relative to the plate body 20.

As opposed to threaded bone screw openings which rigidly engage threads formed along a screw head and limit the surgeon's ability to angle the bone screw relative to the central axis of the threaded opening, the flexible fins 44 engage the anti-back out feature or external thread 17 on the head portion 14 and are structured to allow a degree of angulation of the bone screw 14 relative to the central axis of the bone screw opening 40. In one embodiment, the flexible fins 44 are deflectable or otherwise deformed by the head portion 16 of the bone screw 14 when the bone screw 14 is inserted into and driven through a corresponding one of the bone screw openings 40. As should be appreciated, the flexible fins 44 retain the bone screw 14 in position within the corresponding bone screw opening 40 relative to the plate body 20 to prevent or otherwise inhibit the bone screw 14 from loosening and/or backing out of the opening 40. As the external thread 17 of the bone screw head portion 16 begins to contact the flexible fins 44, the fins 44 engage the external thread 17 to hold the bone screw 14 in place at a desired angle and a desired position, even at angles that are angular offset (i.e., non-parallel) from the central axis of the bone screw opening 40. Engagement between the fins 44 and the external thread 17 securely affixes the bone screw 14 in position relative to the bone plate 12 at a desired position and insertion angle.

In one embodiment, the flexible fins 44 are integrally connected to and protrude radially inward from the inner surface 42 of the bone screw openings 40. In another embodiment, the flexible fins 44 have a thickness that varies in radial direction, and more specifically have a thickness that tapers from a maximum thickness adjacent the inner surface 42 of the opening 40 to a minimum thickness at a terminal end of the fin 44. In a further embodiment, the bone screw openings 40 each have a relatively jagged or undulating inner circumference formed by the inwardly protruding fins 44, and concavities or indentations are formed between adjacent pairs of the fins 44 which extend to a location adjacent the inner surface 42 of the openings 40. Additionally, the fins 44 have a generally round configurations wherein the fins 44 define convex protrusions extending inwardly into the openings 40. In still other embodiments, the fins 44 may be provided in more than one layer (i.e., at more than one level or depth) within the openings 40. The fins 44 may also be provided with a circular shape, a trapezoidal shape, an oval shape, a rectangular shape, a rhomboid shape, a diamond shape, a triangular shape, or other suitable shapes or configurations. The sides or edges of the fins 44 may taper inwardly, outwardly, or may be generally parallel with one another. In some embodiments, each of the bone screw opening 40 are provided with five of the flexible fins 44 protruding radially inward from the inner surface 42. However, it should be understood that the bone screw openings 40 may be provided with one, two, three, four, or six or more of the flexible fins 44. In one embodiment, the flexible fins 44 provide each of the bone screw openings 40 with a star-shaped configuration. However, other shapes and configurations of the bone screw openings 40 and/or the flexible fins 44 are also contemplated, examples of which are described in commonly-owned U.S. Publication No. 2012/0323284 and commonly-owned U.S. Publication No. 2013/0172943, the contents of which are incorporated herein by reference in their entirety.

In the illustrated embodiment, the elongate shaft portion 22 of the plate body 20 includes a first plurality or grouping of the bone screw openings 40, and may also include an elongate slot 50 having a slot length $l_s$ extending generally along the longitudinal axis L, and a slot width $w_s$ extending across a width of the shaft portion 22 transverse to the longitudinal axis L. (FIG. 2). As should be appreciated, the elongate slot 50 is sized for receipt of a bone screw therethrough, with the shank portion of the bone screw anchored within the bone and the head portion of the bone screw positioned within a countersunk region 52 of the elongate slot 50, with the countersunk region 52 opening onto the upper surface 28 of the plate body 20. As should be further appreciated, the bone screw 14 may be displaced along the slot length $l_s$ of the elongate slot 50 during compression of a bone fracture and prior to terminal/definitive tightening of the bone screw 14. The elongate shaft portion 22 may also be provided with at least one additional aperture 54 that is sized for receipt of a pin, an elongate shaft, or a K-wire to provisionally attach the bone plate 12 to the bone prior to anchoring of the bone plate 12 to the bone via the bone screws 14.

Additionally, in the illustrated embodiment, the triangular-shaped head portion 24 of the plate body 20 includes a second plurality or grouping of the bone screw openings 40, and may also include an elongate aperture or slot 60 (also referred to herein as "second elongate slot") extending therethrough. In one embodiment, the elongate aperture 60 has an aperture length $l_a$ extending generally along the longitudinal axis L, and an aperture width $w_a$ extending across a width of the triangular-shaped head portion 24 transverse to the longitudinal axis L. (FIG. 2). In another embodiment, the aperture length $l_a$ of the elongate aperture 60 in the triangular-shaped head portion 24 extends in a direction substantially parallel with the slot length $l_s$ of the elongate slot 50 in the elongate shaft portion 22. In yet another embodiment, the elongate slot 50 in the elongate shaft portion 22 is centered along the longitudinal axis L, and the elongate aperture 60 in the triangular-shaped head portion 24 is laterally offset from the longitudinal axis L. In still another embodiment, the aperture width $w_a$ of the elongate aperture 60 in the triangular-shaped head portion 24 is less than the slot width $w_s$ of the elongate slot 50 in the elongate shaft portion 22. In some embodiment, the elongate aperture 60 is sized for receipt of a K-wire or attachment pin extending therethrough and adapted for anchoring in the bone. As should be appreciated, the K-wire or attachment pin may be displaced along the aperture length $l_a$ of the elongate aperture 60 during compression of a bone fracture and prior to secure engagement of the plate body 20, and more particularly the triangular-shaped head portion 24, to the bone.

In a further embodiment, the triangular-shaped head portion 24 may include at least one fastener opening 62 extending therethrough that does not include the flexible fins 44 or other types or configurations of anti-back out features. The fastener opening 62 can be configured, for example and without limitation, to engagingly receive an orthopedic instrument or device such as a drill guide, an insertion instrument or tool, or other types of device and/or instruments that are used in association with implantation of the bone plate 12 and engagement of the bone plate 12 to the bone. The fastener opening 62 may be provided with a counter bore 64 to facilitate engagement of the instrument, tool or device with the plate body 20.

In another embodiment, the triangular-shaped head portion 24 may further include an elongate visualization window 66 extending therethrough. In the illustrated embodiment, the elongate visualization window 66 is generally centered along the longitudinal axis L and has a shape that is substantially symmetrical relative to the longitudinal axis L. In another embodiment, the elongate visualization window 66 has a window length $l_w$ that extends in a direction transverse to the longitudinal axis L, and preferably in a direction substantially perpendicular to the longitudinal axis L. (FIG. 2). In still another embodiment, the elongate visualization window 66 has a trapezoidal shape. In yet another embodiment, the elongate visualization window 66 is defined by a pair of substantially parallel bases 66a, 66b extending along the window length $l_w$, and a pair of non-parallel legs 66c, 66d that extend substantially parallel with corresponding peripheral side surfaces 37a, 37b of the triangular-shaped head portion 24 of the plate body 20. However, other shapes and configurations of the visualization window 66 are also contemplated including, for example, a rectangular shape, an oval shape, a diamond shape, or other suitable shapes that provide direct visualization of the bone that would otherwise be covered by the bone plate 12, and more particularly the triangular-shaped head portion 24 of the plate body 20 adjacent the radial head of the distal radius. The elongate visualization window 66 preferably remains unobstructed when the plate body 20 is attached to the bone to provide direct visualization of a portion of the bone located beneath the plate body 20.

In still yet another embodiment, the triangular-shaped head portion 24 may include at least one additional pin-receiving aperture 68 sized for receipt of a pin, an elongate shaft, or a K-wire to provisionally attach the bone plate 12 to the bone prior to anchoring of the bone plate 12 to the bone via the bone screws 14. In the illustrated embodiment, the triangular-shaped head portion 24 includes a pair of the pin-receiving apertures 68a, 68b positioned on opposite sides of the longitudinal axis L near the convex distal end surface 38 of the plate body 20.

In the illustrated embodiment of the plate body 20, the elongate slot 50 in the elongate shaft portion 22 and the at least one fastener opening 62 in the triangular-shaped head portion 24 are each centered along the longitudinal axis L. Additionally, in the illustrated embodiment, the first plurality or grouping of the bone screw openings 40 in the triangular-shaped head portion 24 of the plate body 20 are arranged substantially symmetrical relative to the longitudinal axis L, and the second plurality or grouping of the bone screw openings 40 in the elongate shaft portion 22 of the plate body 20 are each substantially centered along the longitudinal axis L. As should be appreciated, the symmetrical layout of the bone screw openings 40 in the plate body 20 allows the same bone plate 12 to be used for right-side and left-side applications.

In a further embodiment of the plate body 20, the first plurality or grouping of the bone screw openings 40 in the triangular-shaped head portion 24 are sized, shaped and configured substantially identical to the second plurality or grouping of the bone screw openings 40 in the elongate shaft portion 22 such that each of the bone screw openings 40 may receive bone screws 14 of the same type and general size.

In still another embodiment of the plate body 20, the elongate shaft portion 22 of the plate body 20 includes two or more of the bone screw openings 40, and the triangular-shaped head portion 24 includes a greater number of the bone screw openings 40 compared to the elongate shaft portion 22. In one specific embodiment, the elongate shaft portion 22 includes three of the bone screw openings 40, and the triangular-shaped head portion 24 includes at least four of the bone screw openings 40. In another specific embodiment, the triangular-shaped head portion 24 includes six of the bone screw openings 40 that are symmetrically arranged relative to the longitudinal axis L of the plate body 20.

Although a particular type and configuration of the bone plate 12 has been illustrated and described herein, it should be understood that other types and configurations of bone plates are also contemplated. For example, other types and configurations of plates are contemplated for use in association with bone other than the distal radius bone. Additionally, other shapes and configurations of openings or apertures extending through the bone plate 12 are also contemplated. For example, the bone plate 12 may be provided with openings or apertures that are smooth or threaded, substantially round, substantially oval, slotted, or having any other suitable shape or configuration.

While the systems and devices disclosed herein have been described for use in the treatment of the distal radius bone, it should be understood that the disclosed systems and devices may also be used in association with the treatment of other bones or bony structures. In reading the claims, words such as "a", "an", "at least one", and "at least a portion" are not intended to limit the claims to only one item unless specifically stated to the contrary. Additionally, when the language "at least a portion" and/or "a portion" is used, the claims may include a portion and/or the entire item unless specifically stated to the contrary. Furthermore, when the term "distal" is used with respect to a structure, the term refers to the far end of the structure, and when the term "proximal" is used with respect to a structure, the term refers to the near end of the structure.

Various changes and modifications to the described embodiments described herein will be apparent to those skilled in the art, and such changes and modifications can be made without departing from the spirit and scope of the invention and without diminishing its intended advantages. Additionally, while the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected.

What is claimed is:

1. A bone plate fixation system, comprising:
   a plurality of bone screws each including a screw head and a threaded shank extending from said screw head and adapted for anchoring within bone; and
   a bone plate extending along a central longitudinal axis and having a plate body defining an outer perimeter that is substantially symmetrical relative to said longitudinal axis, said plate body including an elongate shaft portion and a triangular-shaped head portion extending from said elongate shaft portion;

wherein said plate body includes a number of bone screw openings extending therethrough and each having an inner surface and a plurality of flexible fins integrally connected to and protruding radially inward from said inner surface, wherein said plurality of flexible fins are deflectable by said screw head of one of said bone screws inserted into a corresponding one of said bone screw openings to retain said one of said bone screws in said corresponding one of said bone screw openings relative to said plate body;

wherein said elongate shaft portion of said plate body includes a first plurality of said bone screw openings and an elongate slot having a slot length extending along said longitudinal axis; and wherein said triangular-shaped head portion of said plate body includes:
  a second plurality of said bone screw openings;
  at least one fastener opening extending therethrough that does not include said plurality of flexible fins;
  an elongate visualization window extending therethrough and having a window length extending in a direction transverse to said longitudinal axis; and
  a second elongate slot extending therethrough, the second elongated slot does not include said plurality of flexible fins.

2. The bone plate fixation system of claim 1, wherein said screw head of at least some of said plurality of bone screws includes an external thread adapted to engage with said plurality of flexible fins of a corresponding one of said bone screw openings.

3. The bone plate fixation system of claim 1, wherein said plurality of flexible fins provide each of said plurality of bone screw openings with a star-shaped configuration.

4. The bone plate fixation system of claim 1, wherein said elongate slot has a slot length extending generally parallel with said longitudinal axis.

5. The bone plate fixation system of claim 4, wherein said slot length of said elongate slot in said triangular-shaped head portion extends in a direction substantially parallel with said slot length of said elongate slot in said elongate shaft portion.

6. The bone plate fixation system of claim 1, wherein said elongate slot in said elongate shaft portion is centered along said longitudinal axis; and wherein said elongate slot in said triangular-shaped head portion is laterally offset from said longitudinal axis.

7. The bone plate fixation system of claim 1, wherein said elongate slot in said elongate shaft portion has a slot width; and wherein said elongate slot in said triangular-shaped head portion has a slot width that is less than said slot width of said elongate slot in said elongate shaft portion.

8. The bone plate fixation system of claim 1, wherein said elongate visualization window is centered along said longitudinal axis and has a shape that is substantially symmetrical relative to said longitudinal axis.

9. The bone plate fixation system of claim 1, wherein said elongate visualization window has a window length extending in a direction substantially perpendicular to said longitudinal axis.

10. The bone plate fixation system of claim 1, wherein said elongate visualization window has a trapezoidal shape.

11. The bone plate fixation system of claim 10, wherein said elongate visualization window is defined by a pair of substantially parallel bases extending along said window length, and a pair of non-parallel legs that extend substantially parallel with corresponding peripheral side surfaces defined by said triangular-shaped head portion of said plate body.

12. The bone plate fixation system of claim 1, wherein said elongate visualization widow remains unobstructed when said plate body is attached to the bone to provide direct visualization of a portion of the bone through said plate body.

13. The bone plate fixation system of claim 1, wherein said elongate slot in said elongate shaft portion and said at least one fastener opening in said triangular-shaped head portion are each centered along said longitudinal axis.

14. The bone plate fixation system of claim 1, wherein said second plurality of said bone screw openings in said triangular-shaped head portion are arranged substantially symmetrical relative to said longitudinal axis, and wherein said first plurality of said bone screw openings in said elongate shaft portion are each substantially centered along said longitudinal axis.

15. The bone plate fixation system of claim 1, wherein said second plurality of said bone screw openings in said triangular-shaped head portion are sized, shaped and configured substantially identical to said first plurality of said bone screw openings in said elongate shaft portion.

16. The bone plate fixation system of claim 1, wherein said elongate shaft portion of said plate body includes three or more of said bone screw openings.

17. The bone plate fixation system of claim 1, wherein said triangular-shaped head portion has a convex distal end surface that is substantially centered relative to said longitudinal axis.

18. A bone plate fixation system, comprising:
  a plurality of bone screws each including a screw head and a threaded shank extending from said screw head and adapted for anchoring within bone; and
  a bone plate extending along a longitudinal axis and having a plate body including an elongate shaft portion and a triangular-shaped head portion extending from said elongate shaft portion;

wherein said plate body includes a number of bone screw openings extending therethrough and each having an inner surface and a plurality of flexible fins integrally connected to and protruding radial inward from said inner surface, wherein said plurality of flexible fins are deflectable by said screw head of one of said bone screws inserted into a corresponding one of said bone screw openings to retain said one of said bone screws in said corresponding one of said bone screw openings relative to said plate body;

wherein said elongate shaft portion of said plate body includes a first plurality of said bone screw openings and a first elongate slot having a slot length extending generally parallel with said longitudinal axis; and wherein said triangular-shaped head portion of said plate body includes:
  a second plurality of said bone screw opening;
  a second elongate slot having a slot length extending generally parallel with said longitudinal axis, the second elongated slot does not include said plurality of flexible fins; and
  an elongate visualization window extending therethrough and having a window length extending in a direction transverse to said longitudinal axis.

19. The bone plate fixation system of claim 18, wherein said first elongate slot in said elongate shaft portion is centered along said longitudinal axis; and wherein said second elongate slot in said triangular-shaped head portion is laterally offset from said longitudinal axis.

20. The bone plate fixation system of claim 18, wherein said first elongate slot in said elongate shaft portion has a first slot width; and
wherein said second elongate slot in said triangular-shaped head portion has a second slot width that is less than said first slot width.

21. The bone plate fixation system of claim 18, wherein said plate body defines an outer perimeter that is substantially symmetrical relative to said longitudinal axis.

22. The bone plate fixation system of claim 18, wherein said screw head of at least some of said plurality of bone screws includes an external thread adapted to engage with said plurality of flexible fins of a corresponding one of said bone screw openings.

23. The bone plate fixation system of claim 18, wherein said plurality of flexible fins provide each of said plurality of bone screw openings with a star-shaped configuration.

24. The bone plate fixation system of claim 18, wherein said elongate visualization window in said triangular-shaped head portion of said plate body has a trapezoidal shape.

25. The bone plate fixation system of claim 24, wherein said elongate visualization window is defined by a pair of substantially parallel bases extending along said window length, and a pair of non-parallel legs that extend substantially parallel with corresponding peripheral side surfaces defined by said triangular-shaped head portion of said plate body.

26. The bone plate fixation system of claim 24, wherein said elongate visualization widow remains unobstructed when said plate body is attached to the bone to provide direct visualization of a portion of the bone through said plate body.

27. The bone plate fixation system of claim 18, wherein said first plurality of said bone screw openings in said triangular-shaped head portion are arranged substantially symmetrical relative to said longitudinal axis;
wherein said second plurality of said bone screw openings in said elongate shaft portion are each substantially centered along said longitudinal axis; and
wherein said first plurality of said bone screw openings in said triangular-shaped head portion are sized, shaped and configured substantially identical to said second plurality of said bone screw openings in said elongate shaft portion.

\* \* \* \* \*